United States Patent [19]

Byrom

[11] Patent Number: 5,364,778

[45] Date of Patent: Nov. 15, 1994

[54] COPOLYMER PRODUCTION

[75] Inventor: David Byrom, Cleveland, England

[73] Assignee: Zeneca Limited, London, England

[21] Appl. No.: 103,155

[22] Filed: Aug. 9, 1993

Related U.S. Application Data

[63] Continuation of Ser. No. 624,102, Dec. 10, 1990, abandoned.

[30] Foreign Application Priority Data

Dec. 8, 1989 [GB] United Kingdom ............... 8927791

[51] Int. Cl.⁵ .................... C12P 7/62; C08G 63/06
[52] U.S. Cl. .................... 435/135; 435/244; 435/247; 435/252.1; 435/253.6; 435/829; 528/361
[58] Field of Search ............ 435/135, 244, 247, 253.6, 435/252.1, 829; 528/361

[56] References Cited

U.S. PATENT DOCUMENTS

| | | | |
|---|---|---|---|
| 4,433,053 | 2/1984 | Hughes | 435/829 |
| 4,477,654 | 10/1984 | Holmes et al. | 528/361 |
| 4,788,979 | 12/1988 | Jarrett et al. | 528/361 |
| 4,997,909 | 3/1991 | Doi et al. | 528/361 |
| 5,096,819 | 3/1992 | Page et al. | 435/135 |

FOREIGN PATENT DOCUMENTS

| | | | |
|---|---|---|---|
| 0046344 | 2/1982 | European Pat. Off. | 435/135 |
| 0052459 | 5/1982 | European Pat. Off. | 435/135 |
| 0069497 | 1/1983 | European Pat. Off. | |
| 0124309 | 11/1984 | European Pat. Off. | 435/135 |
| 0204442 | 12/1986 | European Pat. Off. | 435/135 |
| 0288908 | 11/1988 | European Pat. Off. | |

Primary Examiner—Herbert J. Lilling
Attorney, Agent, or Firm—Cushman, Darby & Cushman

[57] ABSTRACT

A microbiological process, and novel bacteria e.g. *Alcaligenes eutrophus* NCIMB 40124, for use in such a process. The process enables the more efficient production of copolymers comprising hydroxyvalerate and hydroxybutyrate monomer units.

9 Claims, No Drawings

COPOLYMER PRODUCTION

This is a continuation of application Ser. No. 07/624,102, filed on Dec. 10, 1990, abandoned.

This invention relates to a microbiological method of producing copolymers comprising 3-hydroxybutyrate (HB) monomer units and 3-hydroxyvalerate (HV) monomer units and to a new micro-organism suitably adapted for use in such a microbiological method.

Homopolymer consisting of HB monomer units, known as polyhydroxybutyrate (PHB) is accumulated by various micro-organisms, principally bacteria, as an energy reserve material as granules within the microbial cells.

PHB extracted from such cells is a thermoplastic polyester of the repeat structure

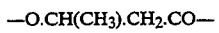
—O.CH(CH₃).CH₂.CO— crystallises to a relatively high level e.g. of the order of 70% or more. This crystallisation behaviour is often disadvantageous when the poller is to be used as, for example, a moulding material.

It is known that the crystallisation of PHB may be modified by incorporation of units of a dissimilar monomer, into the polymer chain and thereby forming a copolymer. Copolymers, comprising HB monomer units and a minor proportion of dissimilar units may be produced by the cultivation of certain micro-organisms, under certain conditions in the presence of certain acids, and alcohols.

Polymers exhibiting an infra-red band said to be indicative of ethylenic unsaturation are described by Davis in "Applied Microbiology" 12 (1964) pages 301 to 304. These polymers which are said by Davis to be copolymers containing 3-hydroxybutyrate units and 3-hydroxy-2-butenoate units, i.e. units of the formula

—O.C(CH₃)=CH.CO— were prepared by cultivating Nocardia on n-butane.

Wallen et al describe, in "Environmental Science and Technology" 6 (1972) pages 161 to 164 and 8 (1974) pages 576 to 579, a polymer melting at 97° to 100° C. (after repeated washing) isolated from activated sludges and containing 3-hydroxybutyrate units and 3-hydroxyvalerate units, i.e.

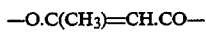
—O.CH(C₂H₅).CH₂.CO— units in the ratio of 1:5.

Marchessault et al reported in "IUPAC Macro Florence 1980 International Symposium on Macromolecules Preprints" 2 (1980) pages 272 to 275 a study of this polymer and confirmed that contained mainly 3-hydroxyvalerate units.

U.S. Pat. No. 3,275,610 describes the microbiological production of polyesters by cultivating certain micro-organisms, especially *Nocardia salmonicolor*, on carboxylic acids containing 4 carbon atoms.

European Patent Specification 0069497 describes the microbial production of a number of polyesters by cultivating certain micro-organisms especially *Alcaligenes eutrophus* mutant NCIB 11599 on suitable substrates.

Published European Patent Application 0204442 describes the microbial production of copolymers of HB and HV by the cultivation of *Alcaligenes eutrophus* mu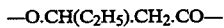tant NCIB 12080 on primary alcohols having an odd number of carbon stores, but excluding methanol.

In order to produce copolymers it known to be necessary to provide a substrate, i.e. a source of energy and carbon, comprising a component that is capable of giving rise to the dissimilar monomer units during at least part of the period when copolymer is accumulated. Thus, for example, in order to produce a copolymer, comprising HB monomer units and HV monomer units, the bacteria are required to be cultivated on a substrate comprising a component from which HV is capable of being synthesised, e.g. propionic acid.

The component that gives rise to the HV monomer units within the copolymer is herein termed the HV component of the substrate.

Specific cultivation conditions are normally needed order to induce PHB production, and accumulation, in known bacteria. Such specific cultivation conditions are also necessary to induce copolymer production, and accumulation.

Some known bacteria produce PHB constitutively, i.e. do not need to be cultivated under specific conditions in order to produce, and accumulate PHB. Nevertheless, unless the aforementioned specific cultivation conditions are employed, even those known strains which produce PHB constitutively may metabolise an HV component such that copolymer is not produced and accumulated.

Furthermore, even when specific cultivation conditions are used, such that copolymer production, and accumulation is induced in known bacteria, only a small proportion of the HV component j s converted by the bacteria into HV monomer units. Thus, the HV component may give rise to non-monomer material, or may be used to synthesise HB monomer units for incorporation into the copolymer, even if the HV component is the sole substrate during the polymer accumulation stage. The metabolism of the HV component, so as to synthesise HB monomer units, may occur to such an extent that significantly less than half of the HV component is converted into the required HV monomer units, and results in the production of copolymers having low percentage levels of HV monomer units.

In order to ensure that at least some of the HV component is converted into the required HV monomer units, and that the required proportion of HV monomer units are present in the copolymer, the bacteria are required to be provided with a large excess of the HV component.

The low conversion efficiency coupled with the relative high expense of the HV component results in a HB/HV copolymer synthesis route that is expensive.

Furthermore, the necessary presence of such a large excess of the HV component in the substrate presents severe problems with conventional microbial routes for copolymer synthesis in that a potentially toxic environment is generated within which the bacteria are required to be cultivated.

We have found that by identifying a major metabolic pathway, for the conversion of HV component to HB monomer units, and by providing strains of bacteria wherein such a pathway is substantially eliminated, it is possible to devise a process in which copolymers are synthesised at high HV component to HV monomer unit conversion efficiencies.

Accordingly, we provide a microbiological process for the production of copolymers comprising HB and HV monomer units using a PHB accumulating bacterium which is not capable of significant growth when cultivated under non growth limiting conditions on a substrate consisting essentially of an HV component, which process comprises cultivating the bacterium in an aqueous medium at a desired weight of dry cells per liter of medium, under growth limitation conditions conducive to the bacterium synthesising and accumulating copolymer, and thereafter harvesting the copolymer containing bacterium wherein the medium comprises a substrate, and the substrate comprises a water soluble assimilable carbon containing HV component and a water soluble assimilable carbon containing HB component.

The process conditions under which the bacterium is cultivated, i.e. temperature, pH, aeration, essential nutrients, may be similar to those commonly used in PHB accumulation processes.

Those essential nutrients required for the growth of the bacterium comprise the following elements, which are normally present in readily assimilable form, normally as water soluble salts: nitrogen, phosphorus, sulphur, potassium, sodium, magnesium, calcium, and iron, together with traces of manganese, zinc and copper.

At least part of the cultivation is conducted under growth limitation conditions, i.e. under conditions wherein an essential requirement for growth but not copolymer accumulation is limited. Under such growth limitation conditions the tendency of the bacterium to produce and accumulate PHB homopolymer is avoided, and the production and accumulation of HV containing polymer is induced. Whilst it may be possible to induce copolymer accumulation by restricting the supply of oxygen to the bacterium, it is preferred to restrict the supply of one or more of the essential nutrients. The most practical elements to limit are nitrogen, phosphorus, or, less preferably, magnesium, sulphur or potassium. The nitrogen may be conveniently supplied in the form of an ammonium salt, whereas the phosphorus may be conveniently supplied as a phosphate.

Where nitrogen limitation is employed, the substrate is preferably nitrogen free and so amide derivatives of the HV component are less preferred. The amount of assimilable nitrogen required is about 10 to 15% by weight of the desired weight of cells less the weight of the accumulated copolymer.

Similar considerations apply, where phosphorus limitation is employed.

Cultivation of the bacterium is preferably conducted so that the dry weight of the copolymer-containing cells is at least 30 g.l$^{-1}$, preferably at least 80 g.l$^{-1}$, and particularly at least 120 g.l$^{-1}$.

The bacterium used is capable of efficiently converting the HV component present in the substrate to HV monomer units. Specifically the bacterium can convert the HV component to HV monomer units at an efficiency, on a molar basis, of greater than 45%, particularly at least 60%, and especially between 70 and 80%, and further advantageously between 80 and 90%.

Preferably, those conditions under which a specific bacterium should be cultivated are those which maximise the efficiency of conversion.

Cultivation of the bacterium preferably comprises a two stage process. In the first stage the bacterium is preferably grown to a certain dry weight per liter, under non-growth limiting conditions on a readily metabolisable substrate, such as a carbohydrate, for example glucose. In the second stage the substrate is at least in part the HV component, and at least one nutrient required for growth is limited, such that the growth limiting conditions exist.

The cultivation may be performed as a batch process, such that copolymer accumulation will occur as the amount of the nutrient required for growth but not copolymer accumulation becomes depleted.

Alternatively, the cultivation may be performed as a continuous process, wherein a stream of culture is removed from the vessel, in which the bacterium is being cultivated, on a continuous or semi continuous basis. The stream removed from the vessel contains bacterium cells in a spent aqueous medium. The spent aqueous medium comprises residual quantities of nutrients and substrate. The flowrate of the stream leaving the vessel corresponds to the rate of addition of fresh aqueous medium to the vessel. The fresh aqueous medium supplied to the vessel contains nutrients and substrate in sufficient amounts to support accumulation of copolymer. Preferably the amount of that nutrient, used to limit the growth of the bacterium, which is fed to the vessel is such that little or none of that nutrient is present in the spent aqueous medium removed from the vessel. Further, it is preferred that the spent aqueous medium is fed to at least one further aerated cultivation stage under batch or preferably continuous or semi-continuous operation, wherein additional copolymer accumulation is stimulated by the addition of fresh HV component containing substrate to the spent aqueous medium. The levels of nutrients and substrate may be adjusted in the spent aqueous medium after leaving the first cultivation stage such that optimum operation of the overall process is maintained.

Alternatively, the cultivation of the bacterium may be conducted as a single stage process. In such a process, wherein copolymer accumulation is induced by limiting the amount of a nutrient required for growth but not for copolymer accumulation, the residence time of the aqueous medium in the vessel is made sufficiently long so as to allow exhaustion of the limiting nutrient, and for copolymer accumulation to occur.

In either a single or multistage process, or in batch or semi continuous or continuous process the HV component may be present as the sole source of carbon present in the substrate during all, or part of, the copolymer accumulation stage, or may be in admixture with other assimilable carbon sources.

The concentration of the HV component in the aqueous medium depends on a number of factors, e.g. whether the process is batch or continuous, the percentage copolymer desired, the percentage of HV monomer units in the copolymer desired. Because the bacterium used is capable of synthesising and accumulating copolymer at high conversion efficiencies, the concentrating of the HV component in the medium to, and hence medium from, the process is relatively low. Generally, the concentration of the HV component at the point of harvest of the bacterium is preferably between 0.1 and 25, and particularly between 5 and 10 g.l$^{-1}$.

The HV component may be propanol, propionic acid, or a salt, ester, anhydride, amide, or halide thereof. Mixtures of compounds suitable for use as HV components may be used.

It is believed that the high conversion of HV component to HV monomer units is made possible because the bacterium cultivated is no longer able to metabolise the HV component to acetyl CoA to a substantial extent.

Although we do not wish to be bound by the following theory, it is thought that the metabolic pathway leading to copolymers comprising HB monomer units and HV monomer units is as follows, in which CoA.SH is unesterified Coenzyme A, CH$_3$.CO.S:CoA is the acetyl thioester of Coenzyme A and is more commonly termed acetyl CoA, NADP is nicotinamide adenine dinucleotide phosphate in the oxidised state, and NADPH$_2$ is reduced NADP.

It is believed that, in the biosynthesis of PHB by a micro-organism, the first step is the synthesis of acetyl CoA. This can be formed for example, from CoA and acetate, or by the decarboxylation of pyruvate, which is the product of the glycolysis of carbohydrates, or which can be formed by decarboxylation of oxaloacetate, the latter being a member of the tricarboxylic acid (TCA) cycle, otherwise known as the Krebbs cycle.

Thus with acetate as the source of acetyl CoA, the PHB is produced by a metabolic pathway involving the reactions:

1. $CH_3.CO.O^- + CoA.SH$—thiokinase→$CH_3.CO.S.CoA + OH^-$
2. $2CH_3.CO.S.CoA$—B ketothiolase→$CH_3.CO.CH_2.CO.S.CoA + CoA.SH$
3. $CH_3.CO.CH_2.CO.S.CoA + NADPH_2$—reductase→$CH_3.CHOH.CH_2.CO.S.CoA + NADP$
4. $CH_3.CHOH.CH_2.CO.S.CoA$—polymerase→$-O.CH(CH_3).CH_2.CO- + CoA.SH$ wherein $CH_3.CO.CH_2.CO.S.CoA$ is acetoacetyl CoA, $CH_3.CHOH.CH_2.CO.S.CoA$ is 3hydroxybutyryl CoA and $-O.CH(CH_3).CH_2.CO-$ is a repeat unit in the polymer.

Thus reaction 4 adds $-O.CH(CH_3).CH_2.CO-$ to a growing polymer chain.

Because of a lack of specificity of the enzymes involved, the corresponding pathway with, for example propionic acid, is thought to be:

1a. $CH_3.CH_2.CO.O^- + CoA.SH$—thiokinase→$CH_3.CH_2.CO.S.CoA + OH^-$

2a. $CH_3.CH_2.CO.S.CoA + CH_3.CO.S.CoA$—B ketothiolase→$CH_3.CH_2.CO.CH_2.CO.S.CoA + CoA.SH$ 3a. $NADPH_2 + CH_3.CH_2.CO.CH_2.CO.S.CoA$—reductase→$NADP + CH_3.CH_2.CHOH.CH_2.CO.S.CoA$ 4a. $CH_3.CH_2.CHOH.CH_2.CO.S.CoA$—polymerase→$-O.CH(C_2H_5).CH_2.CO- + CoA.SH$ wherein $CH_3.CH_2.CO.S.CoA$ is propionyl CoA, $CH_3.CH_2.CO.CH_2.CO.S.CoA$ is 3 ketovaleryl CoA, $CH_3.CH_2.CHOH.CH_2.CO.S.CoA$ is 3 hydroxyvaleryl CoA and $-O.CH(C_2H_5).CH_2.CO-$ is a repeat unit in the polymer.

Thus reaction 4a adds $-O.CH(C_2H_5).CH_2.CO-$ to a growing polymer chain.

As hereinbefore postulated one of the intermediates in the synthesis of an HB monomer unit is itself an intermediate in the synthesis of an HV, it is therefore preferred that the substrate comprises not only an HV component but also a carbon source metabolisable to the required HB monomer intermediate, i.e. an HB component. Thus by controlling the relative amounts in the substrate of components for HB and HV synthesis it is possible to obtain copolymers containing varying proportions of HB and HV monomer units.

A bacterium suitably adapted for use in the process of the present invention may be produced by the mutation of a PHB accumulating strain of *Alcaligenes eutrophus*, and by screening and selecting of the resultant mutants.

Accordingly, we further provide a strain, in particular as a pure culture, of *Alcaligenes eutrophus* designated NCIMB 40124, and mutants and variants derived therefrom.

The strain *Alcaligenes eutropbus* NCIMB 40124 was deposited at the National Collections of Industrial and Marine Bacteria Ltd. (NCIMB), PO Box 31, 135 Abbey Road, Aberdeen AB9 8DG, United Kingdom on the Mar. 24, 1989, under the terms and conditions of the Budapest Treaty.

The strain *Alcaligenes eutrophus* NCIMB 40124, and useful mutants and variants derived therefrom, may be characterised by the following taxonomic description. The strain, and mutants and variants derived therefrom are able to produce and accumulate PHB in a manner similar to that of the parent strain NCIB 12080, produce and accumulate copolymers containing HB and HV monomer units at high HV component to HV monomer conversion efficiencies, grow on a substrate consisting of acetate, but show no grow on a substrate consisting of propionate. The combination of these growth, no growth, and polymer accumulation characteristics distinguish the new strains of *Alcaligenes eutrophus* from existing strains of *Alcaligenes eutrophus*. The evaluation of the growth/no growth characteristics, mentioned above, were conducted under non growth limiting conditions, on a substrate having a carbon content which was provided essentially by the material under test, i.e. acetate or propionate.

Description of *Alcaligenes eutrophus* NCIMB 40124.

Morphology

Gram negative motile rods of approximate size 0.8 $\mu m \times 6.0 \mu m$.

Evidence of intra cellular granules.

No spore formation.

Under a phase contrast microscope occasional subpolar flagella are noted.

Colonial morphology (Lab 8 Nutrient Agar)—the organism is in the form of round, regular, opaque, smooth, white convex colonies. After 3 days the diameter was about 2 min.

A pale brown pigmentation developed with increasing age.

Temperature

At 5° C. no growth.

At 37° C. growth.

At 45° C. no growth.

Characteristics

| | |
|---|---|
| Catalase | + |
| Kovacs Oxidase | + |
| O-F Glucose | very weakly oxidative |
| Pyocyanin | − |
| Fluorescence | − |
| L-Arginine CSU | − |
| Betaine CSU | − |
| Glucose CSU | + |
| Lactate CSU | + |
| Acetate CSU | + |
| CSU Arabinose | − |
| Meso-inositol | − |
| Xylose | − |
| Gas Glucose | − |
| ONPG | − |
| Arginine Moller | − |
| Lysine Moller | − |
| Ornithine Moller | − |
| $NO_3^-$ to $N_2^-$ | − |

| -continued | |
|---|---|
| NO₃ to N₂ | + at 37° C. |
| DNA ase | − |
| Gel stab. | − |
| Gel plate | − |
| Casein | − |
| Starch | − |
| Lecithin egg | − |
| Lipase egg | − |
| NH₃ | weakly positive |
| Indole | − |
| H₂S | − |
| Tween 80 | + |
| Urease | + |

No growth exhibited on methanol at 5 or 14 days.
No growth exhibited on propan-1-ol at 5 or 14 days.
Growth exhibited on acetate at 3 days.
Resistant to penicillin G and streptomycin.
Sensitive to chloramphenicol, tetracycline, polymyxin B and novobiocin (weakly).

Strains of Alcaligenes eutrophus in accordance with the present invention may be produced in a variety of ways, for example, transposon mutagenesis including excision of inserted transposons which are able to cause deletions, chemical mutagenesis using mutagens such as ethane methane sulphonate and mutations caused by invitro manipulation and subsequent recombination.

Strain Alcaligenes eutrophus NCIMB 40124 was prepared in the following manner.

The parent culture was Alcaligenes eutrophus NCIB 12080, available from the National Collection of Industrial and Marine Bacteria Ltd under the terms and conditions of the Budapest Treaty.

The parent culture was grown in mineral salts medium, plus glucose at 1%, to an optical density of 0.9, as measured at 600 nm. A sample (10 mls) of the culture, as grown, was transferred to a 9 cm glass petri dish, and then irradiated with UV light at a dose level sufficient to achieve a kill of 99.9%.

The irradiated culture was transferred to a flask containing mineral salts medium, plus glucose at 1%, and incubated, at 30° C., in the dark for about 16 hours.

10 mls of the incubated culture were then transferred to a flask containing mineral salts medium, plus sodium propionate at 0.075% and D-cycloserine at 800 $\mu$g.ml$^{-1}$. The contents of the flask were then incubated, at 30° C., for about 16 hours.

The culture was then centrifuged, and the resulting pellet resuspended in sterile distilled water.

Serial dilutions were made from the suspension and 0.1 ml aliquots plated from the dilutions onto mineral salts agar containing glucose at 1%. The plates were then incubated and the resulting colonies were replicated plated onto mineral salts agar, containing propionate at 0.075%.

Colonies were identified that were able to grow on the glucose agar plates but not the propionate agar plates. These colonies were selected for further investigation.

The selected colonies of putative mutants were screened for their ability to grow using glucose, or acetate, as a carbon source; their inability to grow on propionate; and their ability to produce and accumulate copolymer, comprising HB monomer and HV monomer units, when supplied with glucose and propionate under nitrogen limited conditions.

One strain produced according to the hereinbefore described procedure is Alcaligenes eutrophus NCIMB 40124.

The process of the present invention is illustrated by the following examples.

EXAMPLE 1

An aqueous medium containing the following, expressed as (g.l$^{-1}$), and having a pH of about 7 (controlled by ammonia addition) was prepared.

| MgSO₄.7H₂O | 2.2 |
|---|---|
| K₂SO₄ | 3.0 |
| Na₂SO₄ | 0.18 |
| FeSO₄.7H₂O | 0.18 |
| Glucose | 13.0 |
| Trace elements | 3.0 (mls) |
| Phosphoric Acid | 6.5 (mls of 1.1M) |

A fermenter containing 3l of the above medium was inoculated with a starter culture of Alcaligenes eutrophus NCIMB 40124. The inoculated medium was incubated, at 30° C., for 24 hours until the phosphate content of the medium became limiting.

Glucose, and propionic acid were then fed to the fermenter at rates of 10 g.hr$^{-1}$, and 3.3 g.hr$^{-1}$ respectively for a further 48 hours.

The cells containing the copolymer were harvested, freeze dried, and analysed for polymer content and composition.

EXAMPLE 2

Example 1 was repeated, except that the flow rates of the glucose and the propionic acid were 6.4 g.hr$^{-1}$, and 0.7 g.hr$^{-1}$, respectively.

Comparative Example 3

Example 1 was repeated, except strain Alcaligenes eutrophus NCIB 12080, was used instead of strain Alcaligenes eutrophus NCIMB 40124.

Comparative Example 4

Example 2 was repeated, except strain Alcaligenes eutrophus NCIB 12080, was used instead of strain Alcaligenes eutropbus NCIMB 40124.

The results of Examples 1 to 4 were as follows:

| Example No. | % HV Component In Copolymer |
|---|---|
| 1 | 29 |
| 2 | 7 |
| C3 | 10 |
| C4 | 5 |

It can thus be seen that the process of the present invention, employing a bacterium according to the invention, can give rise to substantial increase in the conversion efficiency of an HV component into HV monomer units.

I claim:
1. A microbiological process for the production of a copolymer comprising HB and HV monomer units so as to improve the conversion efficiency of an HV component into HB/HV copolymer, said process comprising
   (i) cultivating a PHB accumulating bacterium of the genus Alcaligenes from which a major metabolic pathway for the conversion of HV component to

HB monomer units has been substantially eliminated and which is not capable of significant growth when cultivated under otherwise non growth limiting conditions on a substrate consisting essentially of an HV component, said PHB accumulating bacterium being cultivated in an aqueous medium in which a substrate comprises a water soluble assimilable carbon containing HV component and a water soluble assimilable carbon containing HB component, at a desired weight of dry cells per liter of medium, under growth limitation conditions conducive to said PHB accumulating bacterium synthesizing and accumulating said copolymer, and (ii) harvesting said copolymer containing bacterium.

2. A microbiological process for the production of a copolymer comprising HB and HV monomer units so as to improve the conversion efficiency of an HV component into HB/HV copolymer, said process comprising (i) cultivating a PHB accumulating bacterium from which a major metabolic pathway for the conversion of HV component to HB monomer units has been substantially eliminated and which is not capable of significant growth when cultivated under otherwise non growth limiting conditions on a substrate consisting essentially of an HV component, said PHB accumulating bacterium being cultivated in an aqueous medium in which a substrate comprises a water soluble assimilable carbon containing HV component and a water soluble assimilable carbon containing HB component, at a desired weight of dry cells per liter of medium, under growth limitation conditions conducive to said PHB accumulating bacterium synthesizing and accumulating said copolymer, and (ii) harvesting said copolymer containing bacterium.

3. A process as claimed in claim 1 wherein the concentration of the HV component in the aqueous medium is controlled in order to achieve a desired percentage of HV monomer units in the copolymer.

4. A process as claimed in claim 1 wherein the concentration of the HV component in the medium associated with the harvested bacterium is between 0.1 and 25 $g.l^{-1}$.

5. A process as claimed in claim 1 wherein the HV component is propanol, propionic acid, or an assimilable derivative thereof.

6. A process as claimed in claim 1 wherein the cultivation of the bacterium is conducted so that the dry weight of the copolymer containing cells is at least 30 $g.l^{-1}$.

7. A process as claimed in claim 1 wherein the cultivation of the bacterium comprises a two stage process, such that in a first stage the bacterium is grown to the desired dry weight per liter, under non growth limiting conditions on a readily metabolisable substrate and in a second stage the substrate is at least in part the HV component, and at least one nutrient required for growth is limited, such that the growth limiting conditions exist.

8. A process as claimed in claim 1 wherein the growth limitation conditions are achieved by limiting the amount of assimilable nitrogen and/or phosphorus available.

9. A process as claimed in claim 8 wherein the amount of assimilable nitrogen available is about 10 to 15% by weight of the desired weight of cells less the weight of the accumulated copolymer.

* * * * *